United States Patent [19]
Earhart

[11] Patent Number: 6,077,232
[45] Date of Patent: Jun. 20, 2000

[54] ANTICOAGULANT COMPOSITION

[75] Inventor: Stephen B. Earhart, St. Louis, Mo.

[73] Assignee: Sherwood Services AG, Schaffhausen, Switzerland

[21] Appl. No.: 08/993,369

[22] Filed: Dec. 18, 1997

Related U.S. Application Data

[60] Provisional application No. 60/034,446, Dec. 27, 1996.

[51] Int. Cl.[7] .................................................... A61B 5/00
[52] U.S. Cl. ............................................ 600/573; 600/576
[58] Field of Search ...................................... 600/573, 576, 600/577; 422/99, 102

[56] References Cited

U.S. PATENT DOCUMENTS 4,774,963  10/1988  Ichikawa et al. ..................... 128/763
5,213,765   5/1993  Kasai et al. .

*Primary Examiner*—Max Hindenburg
*Attorney, Agent, or Firm*—Montgomery W Smith; Eric P Raciti; Douglas E. Denninger

[57] ABSTRACT

A blood collection device including a sealed area with a soluvated, non-aqueous anticoagulant composition positioned therein. The preferred anticoagulant composition comprises heparin, polyethylene glycol and optionally, deionized water and one or more salts.

9 Claims, 2 Drawing Sheets

ANTICOAGULANT COMPOSITION

This Appln claims benefit of Provisional Appln No. 60/034,446 filed Dec. 27, 1996.

FIELD OF THE INVENTION

The present invention relates to a proteinase inhibitor anticoagulant composition for use in a blood collection device and a process for the production thereof and more particularly, to a non-aqueous soluvated heparin anticoagulant composition for use in a blood collection device for more rapid dispersement thereof into collected blood.

BACKGROUND OF THE INVENTION

The analysis of whole blood requires the use of an anticoagulant, typically in a collection apparatus, in order to prevent coagulation of a collected blood sample prior to its analysis. Blood collection syringes with dried and unsoluvated or lyophilized heparin anticoagulant are currently sold on the market. Dried unsoluvated heparin alone may not provide adequate anticoagulation function for blood testing purposes due to its slow rate of dispersement in syringes and tubes where the blood and anticoagulant are not easily mixed. This is especially true in long, narrow syringe and tube configurations. Lyophilized heparin is readily dispersed in the blood entering a syringe. However, lyophilization is an expensive, time consuming process requiring the use of costly lyophilizers. Preservation of the heparin in a lyophilized state also requires packaging having very low moisture vapor transmission characteristics. Such packaging tends to be relatively expensive. Accordingly, it would be desirable to have an anticoagulant composition which is inexpensive and readily dispersed throughout blood entering a syringe, tube or like configured blood collection device. Also desirable would be an easily dispersed anticoagulant composition which eliminates the need for an expensive lyophilization process and costly lyophilization equipment. It would also be desirable to have an anticoagulant composition which does not require a preservative and/or low moisture vapor transmission characteristic packaging.

SUMMARY OF THE INVENTION

The present invention relates to a proteinase inhibitor anticoagulant composition which is non-aqueous and soluvated to increase the rate of dispersement thereof throughout collected blood. A blood collection device according to the present invention comprises a long, slender tube, syringe or like blood collection device. Because the preferred embodiments of the present invention are syringes and narrow tubes, for the sake of simplicity throughout this description the subject blood collection device when referred to as a syringe or tube may likewise embody any suitable blood collection device configuration known in the art. The preferred syringe blood collection device of the present invention comprises a barrel of either glass or plastic suitable for pharmaceutical use having a sealable open end designed to accept a plunger portion and a partially closed opposed needle attachment end opposite said sealable open end. The partially closed needle attachment end is formed so as to be capable of accepting a needle attachment portion.

In the preferred syringe embodiment of the present invention, an effective anticoagulant amount of the subject anticoagulant composition is placed within the syringe barrel in a liquid state between the partially closed needle attachment end and the sealable open end. The anticoagulant composition remains in the syringe barrel during blood collection due to its movement within the barrel without expulsion thereof by the plunger portion when the plunger is advanced to a position near the partially closed needle attachment end, i.e., fully forward, and when the plunger portion is withdrawn to draw a blood sample within the syringe barrel.

The anticoagulant composition of the present invention is a solution comprising a proteinase inhibitor and an alcohol such as but not limited to a solution of heparin and polyethylene glycol which optionally may include one or more salts and/or deionized water to control the reactivity of the heparin and/or facilitate the dispensing of the composition, respectively. If deionized water is used in the composition, the deionized water is preferably evaporated after the dispensing of the composition within the syringe barrel. The alcohol which is preferably polyethylene glycol, combined with the proteinase inhibitor which is preferably heparin, prevents the proteinase inhibitor from drying into an unsoluvated state. Heparin in an unsoluvated state dissolves with difficulty and thus requires more time to disperse throughout a collected blood sample.

The present anticoagulant composition though it be free of water, is soluvated with a water miscible alcohol and is capable of rapid dispersement throughout a collected blood sample. This soluvated anticoagulant composition of the present invention shows superior function over heat dried heparin in an unsoluvated state as found in currently marketed blood collection devices. As illustrated by the test results set forth in Chart A below, the use of the anticoagulant composition of the present invention within a blood collection device reduces the anticoagulant solution dispersal time compared to that of dried unsoluvated heparin within a blood collection device so as to be more effective in preventing coagulation within a collected blood sample. The subject anticoagulant composition is likewise less costly to produce than lyophilized heparin also utilized in blood collection devices currently marketed.

DESCRIPTION OF THE DRAWINGS

In the drawings which illustrate the best modes presently contemplated for carrying out the present invention.

DETAILED DESCRIPTION OF THE INVENTION

Figure 1:
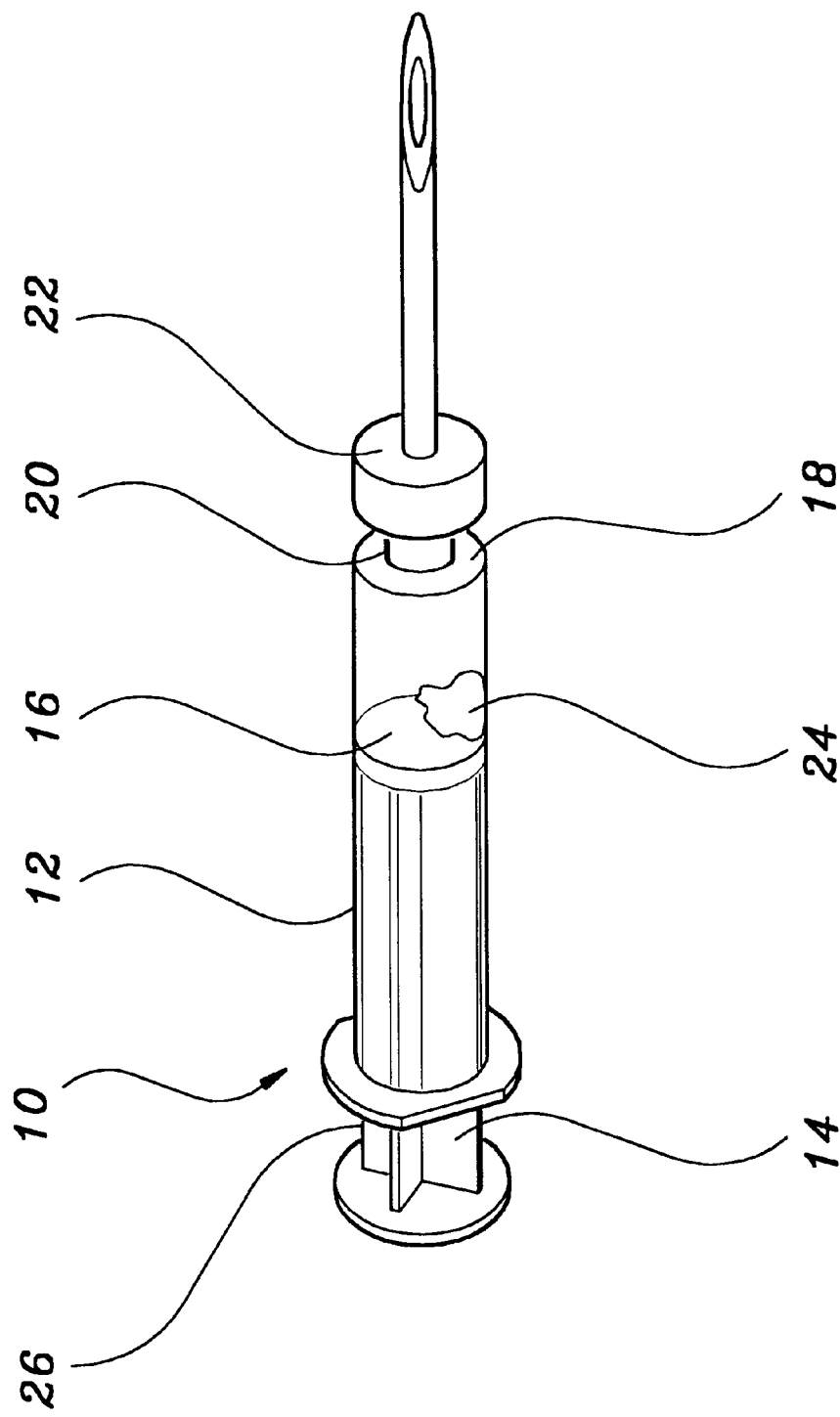
FIG. 1 is a side perspective view of a syringe blood collection device containing the anticoagulant composition of the present invention.
Figure 2:
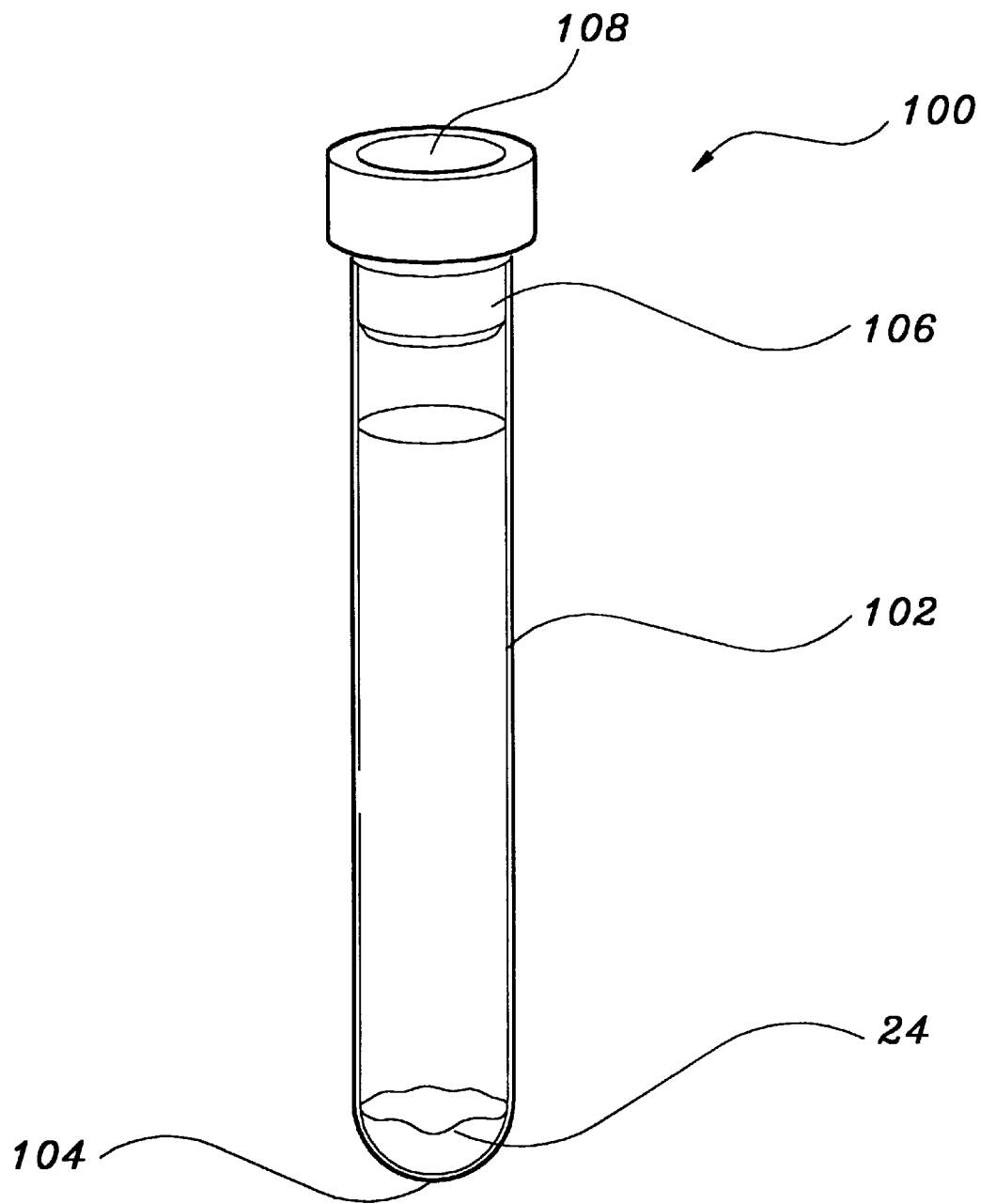
FIG. 2 is a side perspective view of a hermetically sealed tube blood collection device containing the anticoagulant composition of the present invention.

The anticoagulant composition of the present invention is capable of rapid dispersal throughout a collected blood sample and is especially effective for use with blood collection devices of a more long, slender, tubular configuration such as a syringe or hermetically sealed tube as illustrated in FIGS. 1 and 2. The subject soluvated anticoagulant composition eliminates the need for lyophilization and accordingly the use of expensive lyophilization equipment and/or preservatives.

The anticoagulant composition of the present invention is a soluvated non-aqueous solution comprising a proteinase inhibitor such as for example but not limited to a polysaccharide sulfuric acid ester such as for example heparin. The composition also comprises a blend of one or more alcohols such as for example one or more polyhydric alcohols selected from the group consisting of $C_{1-12}$ diols such as glycols and derivatives thereof such as for example ethylene glycol or propylene glycol wherein ethylene glycol is preferred for increased solubility and $C_{1-12}$ polyalkyl diols such as for example polyethylene glycol, polyproplylene glycol or polybutylene glycol wherein polyethylene glycol is preferred for increased solubility and for ready plasticization of the proteinase inhibitor. Optionally, in addition to the proteinase inhibitor and alcohol, the subject anticoagulant composition may comprise one or more salts such as for example calcium, lithium, zinc or potassium but preferably zinc to serve as a chelate to bind the proteinase inhibitor and limit the alteration of electrolyte levels within a collected blood sample. The subject anticoagulant composition may also contain deionized water to dilute the same for easier placement of the fairly viscous composition within a blood collection device. If the composition contains deionized water, the water is preferably removed by evaporation following the placement of the composition within the blood collection device and prior to the use of the device.

A method of producing the anticoagulant composition of the present invention comprises blending a proteinase inhibitor such as for example a polysaccharide sulfuric acid ester such as most preferably heparin with a blend of one or more alcohols. The alcohol blend is preferably a blend of one or more polyhydric alcohols such as those set forth above but most preferably polyethylene glycol for plasticization of the proteinase inhibitor. Optionally, one may likewise add to the proteinase inhibitor prior to the addition of the alcohol, one or more salts such as for example calcium, lithium, zinc or potassium salts but preferably zinc. Deionized water may also optionally be added to dilute the otherwise viscous final composition. The volume of deionized water optionally utilized may vary depending on the desired viscosity of the final anticoagulant composition. A more detailed description of a method of producing the desired anticoagulant composition (Solution B) is set forth in Example 1 below.

The preferred blood collection devices for use with the subject anticoagulation composition of the present invention are illustrated in FIGS. 1 and 2. FIG. 1 illustrates a syringe-style blood collection device generally indicated as 10 having a barrel portion 12, open end 26, plunger portion 14, plunger tip 16, partially closed end 18, needle attachment means 20 and needle attachment 22. An effective quantity of the anticoagulant composition of the present invention is located within barrel portion 12 indicated as 24. FIG. 2 illustrates a hermetically sealed tube-type blood collection device generally indicated as 100 having a tubular body portion 102, closed end 104, sealable open end 106 and stopper 108. An effective quantity of the anticoagulant composition of the present invention is located within tubular body portion 102 indicated as 24.

A method of making the above-described blood collection devices comprises obtaining the blood collection device and placing an effective anticoagulant quantity of the subject anticoagulant composition therein as is described in greater detail in Example 1 below.

An effective quantity of the anticoagulant composition of the present invention was prepared and placed within blood collection devices for comparison effectiveness testing against blood collection devices containing dried unsoluvated heparin as further described in the following example.

EXAMPLE 1

A. Preparation of Anticoagulant Solutions

An anticoagulant solution (Solution A) was made by dissolving 60,000 international units (IU) of heparin, i.e., 0.4918 grams, previously titrated with approximately 0.04 to 0.25 but preferably 0.15 zinc salt in the form of zinc acetate dihydrate in 25 ml of deionized water to obtain 2400 IU/ml heparin. Solution A was then dispensed as a droplet into a corner of the partially closed end 18 of a syringe barrel portion 12.

A second anticoagulant solution (Solution B) which is the anticoagulant composition of the present invention was made by dissolving 60,000 IU of heparin, i.e., 0.4918 grams, previously titrated with approximately 0.04 to 0.25 but preferably 0.15 grams of zinc salt in the form of zinc acetate dihydrate in 25 ml of aqueous media containing deionized water, and 20% weight/volume (w/v) polyethylene glycol 400 (carbowax) to soluvate and plasticize the heparin to obtain 2400 IU/ml heparin. The resulting Solution B was then atomized to place the same within a syringe barrel.

B. Preparation of Syringes

The two heparin solutions prepared as described above were placed in 1 cc blood collection syringes.

In placing Solution A within the syringe barrel, restricted polypropylene tubing was used with a dispensing horn to dispense the same. The flexible polyproplylene tubing was positioned at a corner of partially closed end 18 of barrel portion 12. A pump was activated to dispense an effective anticoagulant amount of Solution A, i.e., 5 microliters, within the blood collection device. The dispensed droplet stayed in contact with a wall of syringe barrel portion 12 and the dispensing tube was then withdrawn from barrel portion 12. The blood collection devices containing Solution A were then dried for two hours at 140° F. after which time Solution A was dry and unsoluvated. Plunger portions 14 having plunger tips 16 were then inserted into open ends 26 of the syringes 10. Approximately 80 syringes were made.

An effective anticoagulant amount, i.e., 5 microliters, of the second solution, Solution B, as described above was placed within syringe blood collection devices using a common ultrasonic dispensing device. Large tubing was used on the inlet side of the small ultrasonic horn portion of the ultrasonic dispensing device in order to prime the pump properly with this fairly viscous solution. Also, a pulsating mode was used for energizing the horn on the ultrasonics apparatus to achieve atomization of the subject heparin-polyethylene glycol solution. Solution B was placed within the syringe barrel portion 12 in a manner so as to attempt to have Solution B settle at the 0.5 cc mark, but the majority settled at the 0.35 cc mark nearer partially closed end 18. The syringes containing Solution B were dried for one hour at 140° F. after which time the subject anticoagulant composition remained a viscous, soluvated material. Although the preferred drying conditions are set forth herein, the drying process could likewise be accomplished by heating the tubes at temperatures within the range of 90 to 200° F. for a period of time ranging between 30 minutes to 4 hours whereby the higher the temperature applied while taking care to not denature the heparin, the less time required for drying. Plunger portions 14 having plunger tips 16 were then inserted into open ends 26 of syringes 10. Approximately 100 syringes were made. All of the syringes containing either Solution A or Solution B after drying were left at room temperature for further processing. Each of the syringes containing either Solution A or B, were pre-siliconized prior to the placement of the particular solution within the barrel.

C. Test Results

Test results obtained from the syringe samples prepared as described above are set forth in Chart A below.

CHART A

Test Results*

| Blood Donor No. | Sample A | Sample B |
| --- | --- | --- |
| 1 | no clot | no clot |
| 2 | clot near plunger | no clot |
| 3 | no clot | no clot |
| 4 | 1 microclot | no clot |
| 5 | clot near plunger | no clot |
| 6 | no clot | no clot |
| 7 | 1 microclot | no clot |
| 8 | 2 microclots | 1 |
| 9 | no clot | 1 |
| 10 | clot near plunger | no clot |
| Total No. Samples | 10 | 10 |
| No. With Microclots | 3 | 2 |
| No. With Clots | 3 | 0 |
| No. Without Clots | 4 | 8 |

*Observations approximately one hour following blood collection

The results of this test, unexpectedly show that the subject anticoagulant composition and more particularly the heparin-polyethylene glycol composition of the present invention reduces the subject anticoagulant composition dispersal time as compared to unsoluvated dried heparin within a blood collection device and is thereby more effective in preventing coagulation within a collected blood sample. The syringes produced in accordance with the above-description with the heparin-polyethylene glycol composition of the present invention disperses readily throughout a blood sample to prevent coagulation of the sample and requires no expensive lyophilization equipment, preservatives or special packaging for the production thereof. Therefore, the blood collection device and anticoagulation composition of the present invention is more effective and/or more economical to produce than the currently marketed unsoluvated or lyophilized configurations currently on the market.

A preferred method of using a blood collection device containing the subject anticoagulant composition comprises drawing a blood sample into a blood collection device by means of a vacuum. In the case of a blood collection device configured as a syringe such as in FIG. 1, the blood sample is drawn into the device by means of a vacuum created by the rearward movement of the syringe plunger portion away from the partially closed end of the device and the blood source. If the blood collection device is a hermetically sealed tube configuration, a vacuum is created and then maintained in the tube by a stopper until a blood sample is drawn within the tube by the vacuum as is well known in the art.

It is shown herein that the present anticoagulation composition provides an effective means by which to inhibit the coagulation of a blood sample within a blood collection device while eliminating the need for lyophilization and costly lyophilization equipment. The present anticoagulant composition, the method of making the present anticoagulant composition, a blood collection device containing the present anticoagulant composition, and the method of making and using a blood collection device containing the present anticoagulation composition as disclosed herein have specific advantages over the heretofore known means of using dried, unsoluvated heparin, dried, unsoluvated and preserved heparin, or lyophilized heparin as an anticoagulant. The subject anticoagulant composition eliminates the need for lyophilization and preservatives, and has improved dispersal time throughout a collected blood sample within a blood collection device. The anticoagulant composition of the present invention is also economical to produce. Hence, for these reasons as well as others, some of which are hereinabove set forth, it is seen that the present anticoagulant composition represents a significant advancement in the art which has substantial commercial significance.

Where there is shown and described herein specific embodiments of the invention, it will be manifest to those skilled in the art that various modifications may be made without departing from the spirit and scope of the underlying inventive concept and that the same is not limited to the particular forms herein described except insofar as indicated by the scope of the appended claims.

What is claimed is:

1. A blood collection device comprising a glass or plastic tubular device sealed to define an enclosed area into which blood may be drawn and an anticoagulant composition located within said enclosed area, whereby said anticoagulant composition includes a proteinase inhibitor and a blend of one or more alcohols.

2. The blood collection device of claim 1 wherein said proteinase inhibitor is a polysaccharide sulfuric acid ester.

3. The blood collection device of claim 1 wherein said proteinase inhibitor is heparin.

4. The blood collection device claims 1, 2 or 3 wherein aid blend is of one or more polyalkyl diols.

5. The blood collection device of claims 1, 2 or 3 wherein said blend is polyethylene glycol.

6. The blood collection device of claim 1, 2 or 3 wherein said device is a syringe.

7. The blood collection device of claim 1, 2 or 3 wherein said device is a hermetically sealed tube.

8. A method of using a blood collection device containing the anticoagulant composition of claim 1, 2 or 3 comprising drawing blood into said device by means of a vacuum.

9. The blood collection device of claims 1, 2, or 3 wherein said blend is selected from the group consisting of diols, diol derivatives and polyyakyl diols.

* * * * *